United States Patent [19]

Karasawa et al.

[11] Patent Number: 4,726,370
[45] Date of Patent: Feb. 23, 1988

[54] RESECTOSCOPE DEVICE

[75] Inventors: Hitoshi Karasawa; Tetsumaru Kubota, both of Hachioji, Japan

[73] Assignee: Olympus Optical Co., Ltd., Tokyo, Japan

[21] Appl. No.: 826,943

[22] Filed: Feb. 7, 1986

[30] Foreign Application Priority Data

Feb. 9, 1985 [JP] Japan .................................. 60-24209
Apr. 26, 1985 [JP] Japan ............................. 60-63567[U]

[51] Int. Cl.⁴ .......................................... A61B 17/36
[52] U.S. Cl. .................................... 128/303.15; 128/6
[58] Field of Search ........................................ 128/4–8, 128/303.1, 303.13–303.17

[56] References Cited

U.S. PATENT DOCUMENTS

| | | | |
|---|---|---|---|
| 1,963,636 | 6/1934 | Wappler | 128/303.15 |
| 2,008,525 | 7/1935 | Wappler | 128/303.15 |
| 3,939,839 | 2/1976 | Curtiss | 128/303.15 |
| 4,060,086 | 12/1977 | Storz | 128/303.15 |
| 4,134,406 | 1/1979 | Iglesias | 128/303.15 |
| 4,149,538 | 4/1979 | Mrava et al. | 128/303.15 |
| 4,506,668 | 3/1985 | König | 128/303.15 |
| 4,538,610 | 9/1985 | Kubota | 128/303.15 |

FOREIGN PATENT DOCUMENTS

2835649 3/1979 Fed. Rep. of Germany .

*Primary Examiner*—Max Hindenburg
*Attorney, Agent, or Firm*—Armstrong, Nikaido, Marmelstein & Kubovcik

[57] ABSTRACT

A resectoscope device comprises a sheath body having an elongated hollow sheath to be inserted into a urethra. A handle part has a slider connected to the sheath body and slides in the axial direction. An observing scope is inserted into the sheath through the handle part and sheath body. An electrode is inserted through the sheath, and is removably connected at the rear end to the slider. The electrode has a resecting part that can be projected out of and retreated into a beak opening at the tip of the sheath by the sliding operation in the axial direction of the slider. A stabilizer is provided in the electrode and the scope is able to be inserted therethrough so that a forked part of the electrode may be housed in contact with the inner peripheral surface of the beak and the resecting part may be housed without catching on the beak opening. A spacer which holds the stabilizer constant with respect to the inside surface of the sheath, is provided to set the scope, electrode means and handle without inclining them with respect to the inside surface of the sheath.

5 Claims, 23 Drawing Figures

RESECTOSCOPE DEVICE

BACKGROUND OF THE INVENTION

1. Field of the Invention

This invention relates to a resectoscope device to be inserted into a bladder through a urethra to scrape and resect the endogland of a prostate swollen by a prostate swelling disease or the like off the exogland.

2. Related Art Statement

Recently there is extensively used an endoscope which can be inserted in the insertion part into a body cavity to observe, diagnose and cure an affected part or the like. In such an endoscope, there is a resectoscope device formed to be inserted into a bladder through a urethra so that a prostate can be resected or operated on by passing a high frequency current through a resecting electrode means.

Generally, a resectoscope device comprises a hollow resectosheath to be inserted through a urethra, a handle part having a slider removably fitted to the rear end side of the resectosheath and an observing scope removably fitted from the rear end side of the handle part and has an electrode means forked and looped at the tip to resect a prostate so as to be inserted through the above mentioned resectosheath and to be fixed at the rear end to the slider so that the resecting part at the tip of the electrode means may be projected out of and retracted into the tip of the resectosheath.

Now, in the conventional resectoscope, the positional relation of the inside surface of the sheath with the electrode means, scope and handle is not kept constant. Therefore, the insertion part of the handle, in which the scope and electrode means are inserted and combined within the sheath, will not be parallel with the axial direction of the sheath but will be inclined, the visual field of the scope in the tip part of the sheath will be eclipsed, the entire operation field will not be able to be fully observed and the operation will be obstructed from being safely and efficiently made. There has been also a problem that, due to the above mentioned inclination, the resecting part at the tip of the electrode means may catch on a beak opening at the tip of the sheath so as to be immovable or may be broken.

In order to solve the above mentioned problems, the visual field angle is narrowed to prevent the visual field from being eclipsed or the dimension of the resecting part is made small to prevent being caught on the beak opening. However, thereby, the efficiency of the operation will be reduced and the operating time will become longer. Thus, it is not an effective solution.

U.S. Pat. No. 4,134,406 discloses a cylindrical stabilizer for inserting a scope in the axial direction provided on the way of an elongated electrode means inserted within a sheath. However, this prior art example is effective to guide the scope so as to parallel with the axial direction of the electrode means but can not make the scope parallel with the axial direction of the inside surface of the sheath.

In U.S. Pat. No. 3,939,839, it is disclosed that a metal leg of a fixed height for holding the handle in a fixed position with respect to the inside surface of the sheath is provided below the insertion part of the handle with a view to making the joint of the sheath body with the handle water-tight. However, in this prior art example, when the positional relation between the inside surface of the sheath and the handle is directly determined, the above described problem with the insertion part of the handle, in which the scope and electrode means are inserted and combined, inclines with respect to the axial direction of the inside surface of the sheath, can be effectively prevented. However, the handle is to be used in common with sheathes of various thicknesses. If the thickness of the sheath is different, the positional relation between the insertion part of the handle and the inside surface of the sheath will naturally vary. Therefore the sheath of the thickness of the inside diameter, in which the tip of the above mentioned metal leg just contacts the inside surface of the sheath will work but, with the sheath of an inside diameter thicker than that, the same problem as is described above will occur.

Further, in the resectoscope device disclosed in U.S. Pat. No. 4,060,086, the forked part on the tip side of the shaft part of the electrode is inclined to the upper side so that the looped resecting part at the tip of the electrode means will not catch on the beak opening when the handle is operated. However this electrode means is fixed only on the handle side, is likely to be influenced by the slightest backlash or the like on the handle side and is difficult to actually set or hold in this state. Even if the electrode means is set in a proper inclined state, in case it is pressed against an affected part to be resected, it will be deformed and, when it is disassembled after being used, it will be likely to be varied from the proper inclined state by the operation and will have to be readjusted.

OBJECTS AND SUMMARY OF THE INVENTION

An object of the present invention is to provide a resectoscope device wherein a resecting part at the tip of an electrode means is prevented from catching on a beak opening without reducing the resecting function and is therefore prevented from being broken from being caught on the beak opening.

Another object of the present invention is to provide a resectoscope device wherein a scope, electrode means and handle, when combined with a sheath of a different inside diameter, can be set without being inclined to the inside surface of the sheath and the visual field of the scope can be prevented from being eclipsed to secure the operation visual field and to make the operation safe and efficient.

A further object of the present invention is to provide a resectoscope device wherein the insertion part of a handle, to be inserted into a sheath, can be prevented from inclining to the axial direction of the inside surface of the sheath and the joint of the sheath body with the handle can be positively held water-tight.

A feature of the present invention is that a stabilizer, through which a scope can be inserted, is provided in an electrode means and a forked part, on the tip side of an electrode means, is inclined to the forward upper side with respect to a shaft part to be inserted through a sheath so that, when a resecting part formed on the tip side of the forked part is to be retreated into a beak opening, the forked part will be housed in contact with the inner peripheral surface of the beak on the side above the center axis of the sheath to prevent the resecting part from catching on the beak opening.

Another feature of the present invention is that a stabilizer, constant with respect to the inside surface of a sheath and setting an electrode means and scope at a fixed spacing with respect to the inside surface of the sheath, is provided to set the scope, electrode means and handle when combined with the sheath of a different inside diameter, without inclining to the inside surface of the sheath.

The other features and advantages of the present invention will be made clear enough with the following explanation.

BRIEF DESCRIPTION OF THE DRAWINGS

FIGS. 1 to 5 relate to the first embodiment of the present invention.

FIGS. 6 and 7 relate to the second embodiment of the present invention.

FIGS. 10 to 14 relate to the fifth embodiment of the present invention.

FIGS. 15 to 18 relate to the sixth embodiment of the present invention.

DETAILED DESCRIPTION OF PREFERRED EMBODIMENTS

Figure 2:
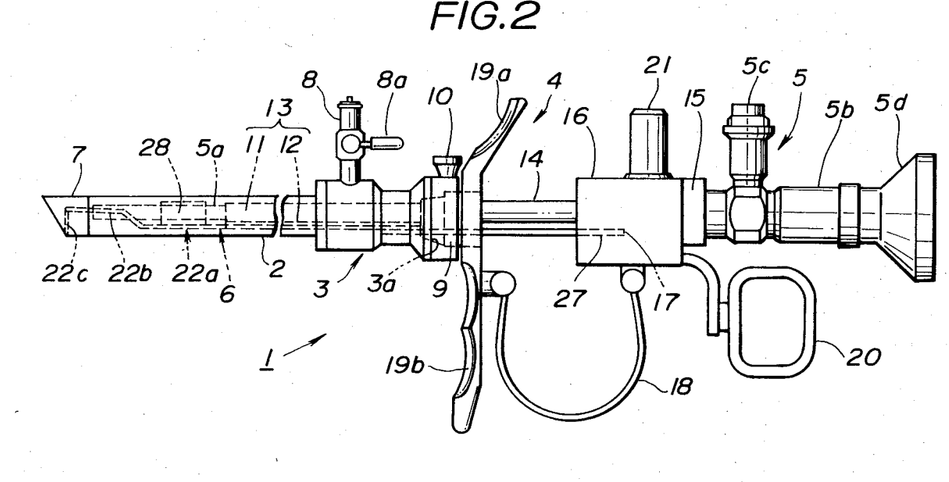
FIG. 2 is a side view showing a resectoscope device of the first embodiment.

As shown in FIG. 2, a resectoscope device 1 of the first embodiment is formed of an assembly of a sheath body 3 forwardly connected with an elongated sheath 2 to be inserted into a urethra, a handle 4 connected to the sheath body 3, an observing scope 5 inserted through the sheath 2 from the rear of the handle 4 and an electrode means 6 inserted through the sheat 3 from the above mentioned handle 4. The above mentioned sheat 2 is provided with an insulating beak 7 connected to the tip of the sheath. This sheath 2 may be formed of an insulating material integrally with the beak 7. The above mentioned sheath body 3 has a water feeding port 8 fitted with a cock 8a feeding an irrigating liquid into a bladder through the sheath 2. The body 3 also has a fitting port 3a fitting a joint 9 of the handle 4 formed to engage, for example, a click mechanism to fix the joint 9 of this handle within the fitting port 3a.

The handle 4 is connected forward of the joint 9 and is provided with a scope guide pipe 11 through which the insertion part 5a of the scope 5 is inserted and an electrode means guide pipe 12 through which the electrode means 6 is inserted. This insertion part 13 is inserted into the sheath 2. The joint 9 of the handle 4 is provided with a guide shaft 14 projecting rearward in the axial direction. A scope joint 15 is fixed to the rear end of this guide shaft 14. On the other hand, a slider 16, sliding in the axial direction along the guide shaft 14, is arranged between the above mentioned forward joint 9 and rearward scope joint 15 and is energized to return to contact, for example, the rearward scope joint 15 by a spring 18 provided between the slider 16 and forward joint 9. The above mentioned spring 18 is an arcuate plate spring in the illustrated example but may be a coil spring or may not be provided. The joint 15 of the above mentioned handle 4 is provided with finger hangers 19a and 19b projecting respectively above and below. The slider 16 has also a thumb hanging ring 20 behind the below the slider 16.

The above mentioned slider 16 has an electrode fixing part 17 in which the electrode means 6 is inserted at the rear end from the front to be removably fixed. This connected electrode means 6 is provided with a connector 21 projecting to have a high frequency current passed through the electrode means 6 from a high frequency cautery current source not illustrated. The electrode means 6 fixed to the slider 16 and provided to project forward is to project forward through an inserting hole formed in the joint 9 of the handle 4 and the electrode means guide pipe 12 provided to project forward from the joint 9.

The scope joint 15 of the handle 4 is to removably insert and connect the scope 5. The connected scope 5 is to be inserted through the above mentioned scope guide pipe 11 provided to extend to the rearward scope joint 15 from the forward joint 9 and to be projected forward of the pipe 11. In the illustrated example, the rearward extended portion of the scope guide pipe 11 is also the guide shaft 14. However, this guide shaft may be separately provided. The above mentioned scope 5 is formed of a body 5b, an elongated insertion part 5a provided to be connected forward, a light guide connector 5c and an eyepiece 5d. Within this scope 5, there are arranged light guide fibers leading an illuminating light to the tip of the insertion part 5a and an image transmitting optical system transmitting an observed image to the eyepiece 5d from the tip of the insertion part 5a.

Figure 1:
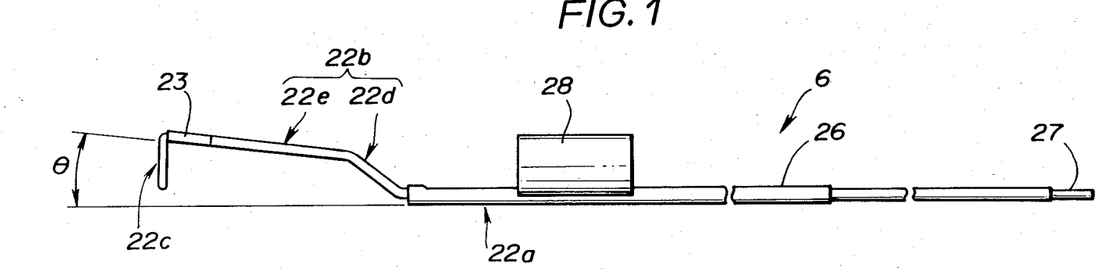
FIG. 1 is a side view showing an electrode means of the first embodiment.
Figure 3:
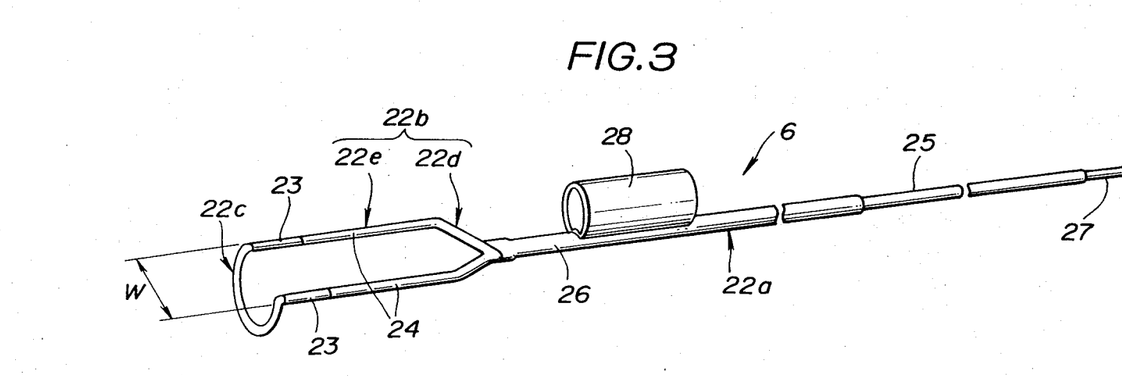
FIG. 3 is a perspective view of the electrode means in FIG. 1.

The electrode means 6 to be a main component of the first embodiment is made as shown in FIGS. 1 and 3.

The electrode means 6 is formed of a shaft part 22a which is inserted through the sheath 2, a forked part 22b forked on the tip side of the shaft part 22a and a resecting part 22c formed to be an arcuate loop by bending the tip of the forked part 22b downward substantially at right angles with the shaft part 22a. This resecting part 22c is to be fed with a high frequency current from a current source not illustrated so that an affected part (such as a prostate gland) contacted by this resecting part 22c can be resected or cut open or bleading can be stopped.

The above mentioned forked part 22b in the part (indicated by 22d and noted as a branched part)

branched from the shaft part 22a and leading to parallel bars, having a predetermined spacing W; is bent upward (in case it is inserted eccentrically downward through the sheat 2) at a comparatively large angle with the axial direction of the shaft part 22a as shown iin FIG. 1. The parallel branch parts 22e, parallel with each other, are projected forward upward at a small angle $\theta$ with the shaft part 22a and the resecting part 22c is formed at their tips. The forked part 22b, in the rear adjacent to the resecting part 22c of bare conductors, is coated with insulating tubes 23, 23. The insulating tubes 23, 23, except for the parts on the tip sides, are reinforced by being further covered with pipes 24, 24 or the like. The the bare conductors forming the resecting part 22c and coated with the insulating tubes 23, 23 on the way are integrally made and are connected with the conductor of the shaft part 22a.

On the other hand, the shaft part 22a is formed of a shaft pipe 26 which coats the conductor electrically connected with the bare conductors of the resecting part 22c, with an insulating tube 25 and further covering and reinforcing this insulating tube 25 to prevent deformation or the like. A slider joint 27 is fitted by exposing the conductor in the rear end part and inserting it into the electrode means fixing part 17 of the slider 16.

On the above mentioned electrode means 6, a stabilizer 28, cylindrical along the axial direction above the shaft pipe 26, is fixed by soldering, brazing or bonding near the tip side of the shaft pipe 26 to prevent the rotary twisting of the entire electrode means 6 so that the electrode means 6 can be smoothly moved forward and rearward.

This stabilizer 28 is formed of material such as a metal or plastic so that the insertion part 5a of the scope 5 can be inserted through the substantially cylindrical inside. When the slider joint 27 at the rear end of the electrode means 6 is fixed to the slider 16, if the slider 16 is moved forward and rearward, the stabilizer 28 will contact, for example, on the upper outer periphery of the stabilizer with the inner peripheral surface of the sheath 2 so as to be movable forward and rearward. Further, by this forward and rearward movement, the resecting part 22c can be projected forward out of the opening of the beak 7 and retreated into the beak 7.

Figure 4:
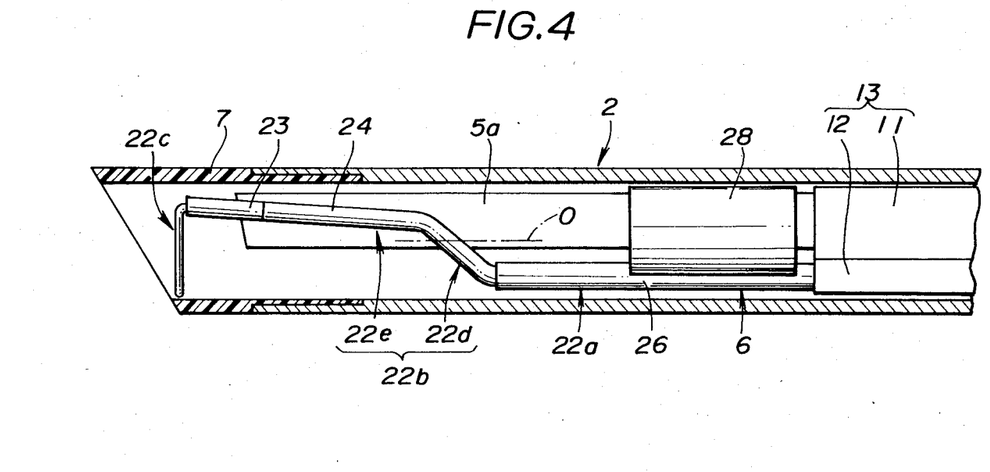
FIG. 4 is a sectioned view showing the tip side of the resectoscope device in FIG. 2 as magnified.

The forked part 22b as connected to the tip side of the shaft part 22a of the above mentioned electrode means 6 is inclined to project forwardly upward so that, when the electrode means 6 is to be used, the boundary positions of the forked parallel parts 22e with the branched part 22d will be above the center axis position (indicated by a sign 0 in FIG. 4) of the sheath 2. In this case, the distance (spacing) W between the forked parallel parts 22e can be set to be of the size of about the inside diameter of the sheath 2 (beak 7) so as to be able to develop the resecting function.

Therefore, when the shaft part 22a of the above mentioned electrode means 6 is inserted on the rear end side through the sheath 2 and is fixed to the electrode fixing part 17 of the slider 16, if the slider 16 is pulled rearward to house (retreat) the resecting part 22c into the sheath 2, the spacing W in the horizontal direction (lateral direction) of the forked parallel parts 22e will become larger than the lateral width inside the sheath 2 (the beak 7 at the tip) (near the boundaries of the forked parallel parts 22e with the branched part 22d when the amount of insertion into the sheath 2 is large, the height of the forked parallel parts 22e in the opening of the beak 7 will gradually become larger, therefore, the width in the horizontal direction of the beak 7 in this high position will become relatively smaller than the diameter and the above mentioned state will be likely to be made) but the forked parallel parts 22e and resecting part 22c will be able to be housed into the beak 7.

That is to say, in case the slider 16 is moved rearward to house the resecting part 22c into the opening of the beak 7, the forked parallel parts 22e will be relatively pressed substantially in the shoulder parts, that is, in the obliquely upper outer peripheral positions by the inner peripheral surface of the beak 7 above the center position of the beak 7 and, by this pressing, the spacing W in the lateral direction of the forked parallel parts 22e will be narrowed and the resecting part 22c will be positively housed into the beak 7. In such a case, if the resiliency of the forked part 22b is made proper and the sliding on the inner periphery of the beak 7 is improved (the friction coefficient is reduced), the forked parallel parts 22e will be narrowed and displaced upward and the resecting part 22c will be prevented from catching at the lower end on the peripheral edge of the opening of the beak 7 so as to be able to be effectively housed.

Figure 5:
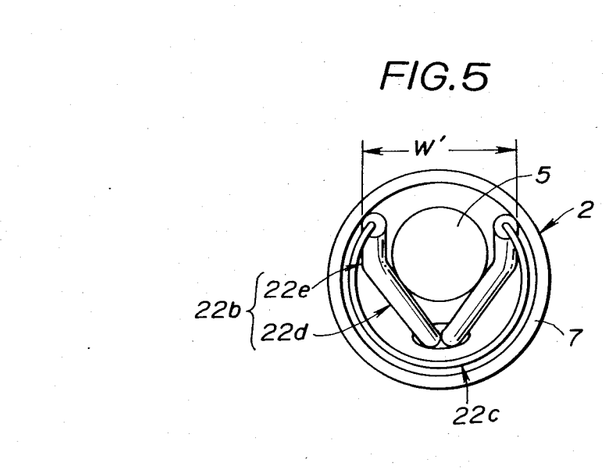
FIG. 5 is a magnified elevation showing the tip side of the electrode means in FIG. 4 as housed.

FIG. 5 shows the resecting part 22c as housed when the forked part 22b is pressed by the inner peripheral surface of the beak 7 so as to be of a width W' (W>W') narrower than the spacing W before the housing.

According to the thus formed first embodiment, the forked part 22b of the electrode means 6 is bent upward on the rear end side reversely to the shaft part 22a which is inserted displaced eccentrically downward in the sheath 2. The forked part 22b is further bent downward at the tip substantially at right angles to form the resecting part 22c. The forked parallel parts 22e are inclined upward so as to be eccentrically displaced reversely to the bending direction of the resecting part 22c more on the tip sides than on the rear end sides. Therefore, even in case the spacing W of the resecting part 22c is set to be about the inside diameter of the sheath 2 to improve the resecting function, when the forked parallel parts 22e are to be housed into the sheath 2 (beak 7) by the operation of the slider 16, the forked parallel parts 22e will be pressed by the inner peripheral wall surface of the beak 7 so as to be narrowed and housed. That is to say, even if there is any backlash between the sheath 2 and the joint 9 of the handle 4, if the slider 16 is operated to retreat the resecting part 22c into the beak 7, the forked parallel parts 22e will be pressed by the inner peripheral surface of the beak 7 to narrow the spacing W in the horizontal direction and will be housed into the beak 7.

Therefore, when such treatment as resection is made with the resecting part pressed against an affected part, even if the resecting part 22c is more or less deformed to expand the width, by the retreating operation, the width will be able to be narrowed and therefore the resecting part 22c will be able to be effectively prevented from catching on the opening of the beak 7.

Figure 6:
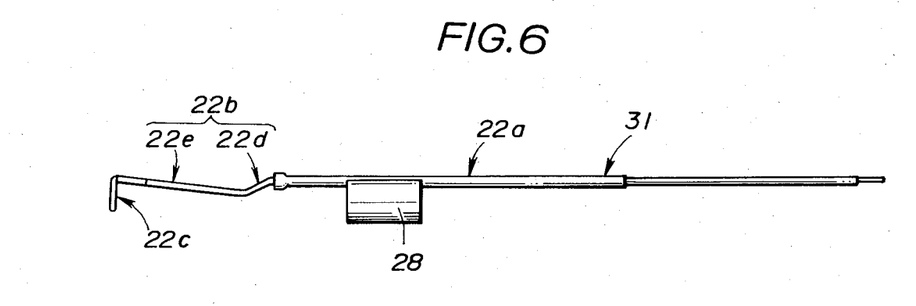
FIG. 6 is a side view showing an electrode means in the second embodiment.

FIG. 6 shows an electrode means 31 relating to the second embodiment of the present invention.

The electrode means 31 in this second embodiment is shown to be inserted as eccentrically displaced above the centerline of the shaft part 22a (sheath 2). The stabilizer 28 is fitted below the centerline near the tip side of the shaft part 22a. In the forked part 22b provided as connected to the tip of the shaft part 22a, the branched part 22d is inclined (bent) forward downward and then the forked parallel parts 22e are gradually inclined forwardly upward and have the resecting part 22c formed at the tips.

Figure 7:
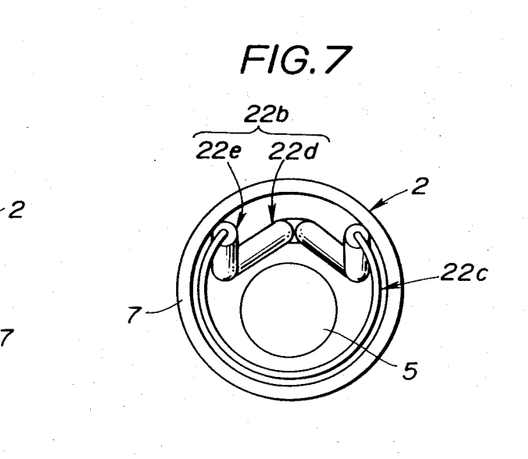
FIG. 7 is an elevation showing the tip side of the electrode means in the second embodiment as housed.

This electrode means 31 as housed in the beak 7 (as the elevation in FIG. 4 corresponding to FIG. 5) is as shown in FIG. 7.

In this case, too, if the slider 16 is operated to retreat the resecting part 22c, the forked parallel parts 22e will be relatively pressed by the inner peripheral wall surface above the center position of the beak 7 to narrow the width and will be housed into the beak 7.

The operation and effect of this second embodiment are substantially the same as of the above mentioned first embodiment.

Figure 8:
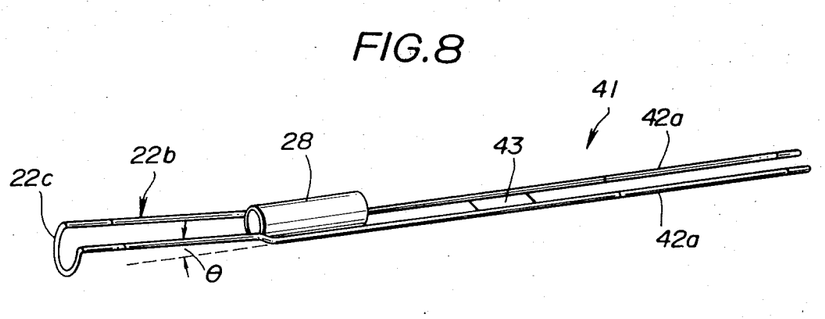
FIG. 8 is a perspective view showing an electrode means in the third embodiment of the present invention.

FIG. 8 shows an electrode means 41 relating to the third embodiment of the present invention.

In this electrode means 41, the shaft part 22a in the electrode means 6 of the first embodiment is formed of parallel shafts 42a, 42a having a plate 43 holding the spacing at a predetermined value fitted in between. The forked parallel parts 22b are formed of only forked parallel parts having no branched part and are inclined forwardly upward at a proper angle, for example, with the parallel shafts 42a, 42a. In this case, the boundaries of the forked parallel parts 22b with the tip part (resecting part 22c) are so set as to be above the center position of the beak (even if there is any deformation or any backlash in the connection of the handle with the sheath). Therefore, if the electrode means 41 is retreated, the resecting part will be pressed to be narrowed and will be housed.

The operation and effect of this third embodiment are substantially the same as of the above mentioned first embodiment. The spacing of the forked parallel parts 22b may be made larger than of the parallel shafts 42a, 42a.

Figure 9:
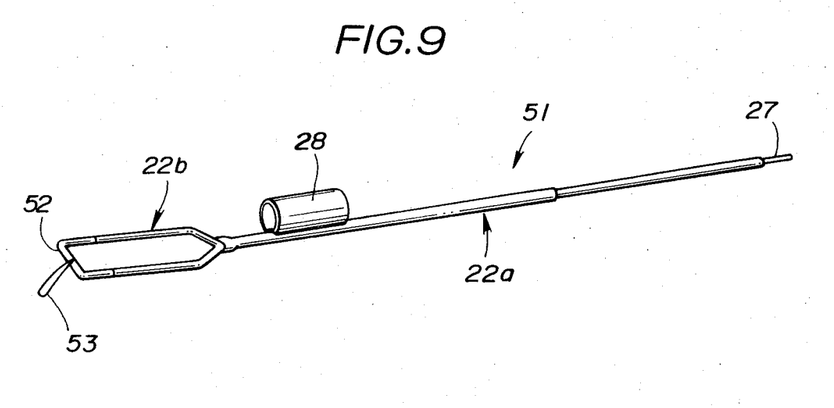
FIG. 9 is a perspective view showing an electrode means in the fourth embodiment of the present invention.

FIG. 9 shows an electrode means 51 relating to the fourth embodiment of the present invention.

In this electrode means 51, the resecting part 22c formed at the tips of the forked parallel parts in the above mentioned first embodiment is not in the form of a loop but is in the form of a knife. That is to say, the forked parallel parts 22e are extended at the tips to be turned inward to form a side 52 in the form of a channel and a forward downward projecting knife 53 is formed in the middle part of the side 52 so as to be a resecting part. In this case, it is preferable to make the resiliency of the side 52 small (to make the resiliency constant small in order to be soft) so that the width may be variable. Also, the side 52 may be made arcuate so that the width may be variable.

The resecting part in the present invention may be in any other form than is described above.

When more than half of the forked part 22b in the lengthwise direction is displaced above the center position of the beak, the width will be able to be effectively narrowed while retreating the resecting part. However, the present invention is not limited to this but includes at least the tip part eccentrically displaced above the center position of the beak. When the resecting part is bent upward or is inclined upward, the forked part may be eccentrically displaced below the center position of the beak.

FIGS. 10 to 14 relate to the fifth embodiment of the present invention. An electrode means 61 in this embodiment is formed of the shaft part 22a to be inserted through the sheath 2, the forked part 22b forked on the tip side of this shaft part 22a and the resecting part 22c having an arcuate loop formed by downward bending the forked part 22b at the tip substantially at right angles with the shaft part 22a.

Figure 10:
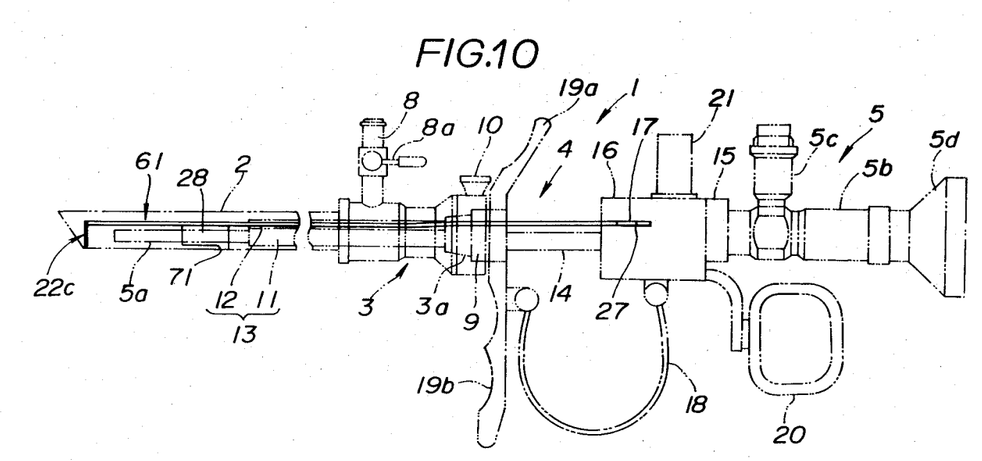
FIG. 10 is a formation view of the entire assembly.
Figure 11:
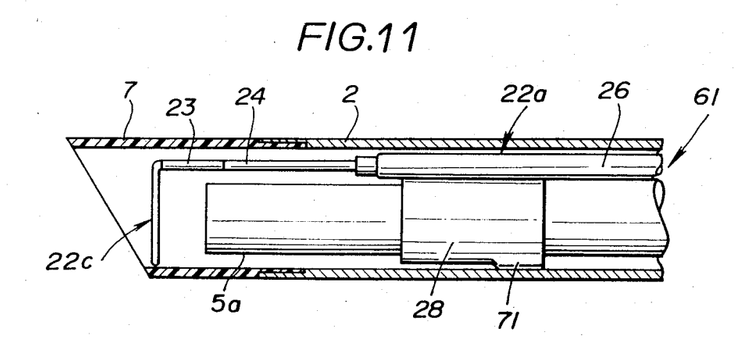
FIG. 11 is a sectioned view showing the tip side of the entire assembly in FIG. 10 as magnified.

On the other hand, the same as in the second embodiment, the stabilizer 28 is fitted below the centerline near the tip side of the above mentioned shaft part 22a. Below the outer periphery of this stabilizer 28, a spacer 71 is formed to project, for example, integrally in the axial direction. This spacer 71 is set to project an amount such that the spacer 71 contacts the inside surface of the sheath and is combined with the handle 4 and the electrode means 61 and scope insertion part 5a inserted through the insertion part 13 of the handle 4 are held in a fixed position relation (ideally in parallel) with respect to the axial direction of the inside surface.

That is to say, this spacer 71 is slid in the axial direction always in contact with the inside surface of the sheath. The electrode means 61 and scope insertion part 5a are kept at a fixed spacing always set with respect to the inside surface of the sheath 2 or preferably in parallel so that the inclination of the electrode means 61, scope insertion part 5a and handle insertion part 13 within the sheath 2 may be prevented.

Figure 12:
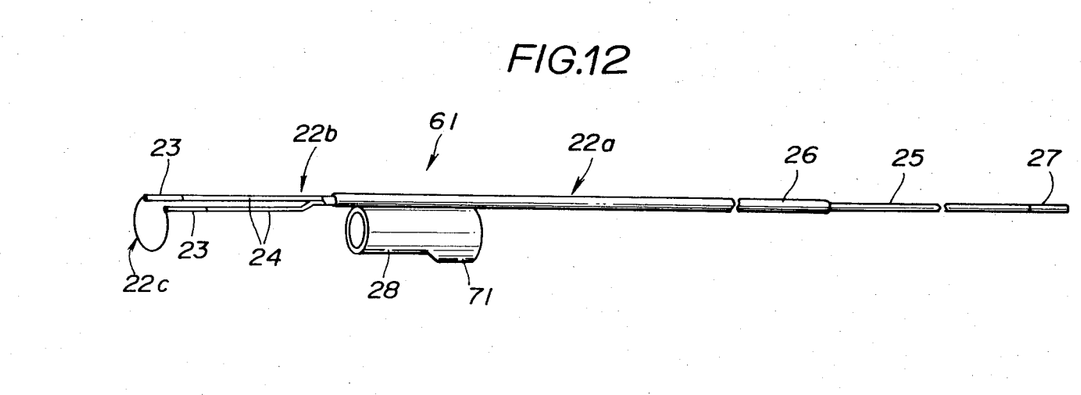
FIG. 12 is a perspective view showing an electrode means.
Figure 13:
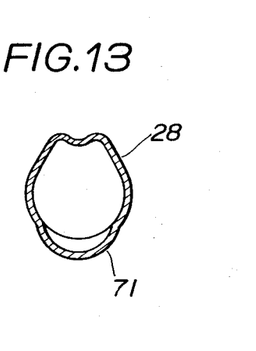
FIG. 13 is a sectioned view of a stabilizer part of the electrode means.

In the above mentioned FIGS. 12 and 13, the spacer 71 formed by modifying a part of the rear end side of the substantially cylindrical stabilizer 28 is shown. However, this spacer may be formed by modifying a part of the front and rear ends of the stabilizer 28 or by modifying the lower part of the stabilizer 28 over the entire length.

Figure 14A:
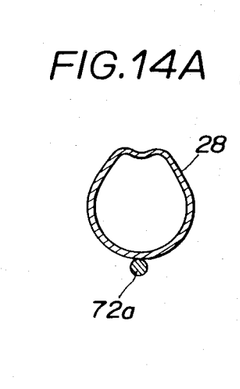
FIGS. 14(A) to (C) are sectioned views showing modifications of a spacer provided in the stabilizer.
Figure 14B:
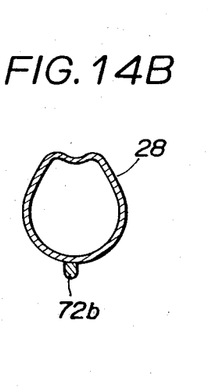
Figure 14C:
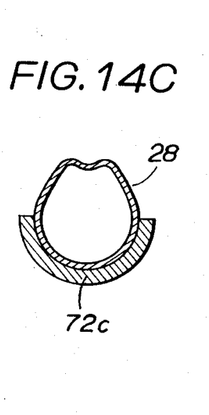
Figure 15:
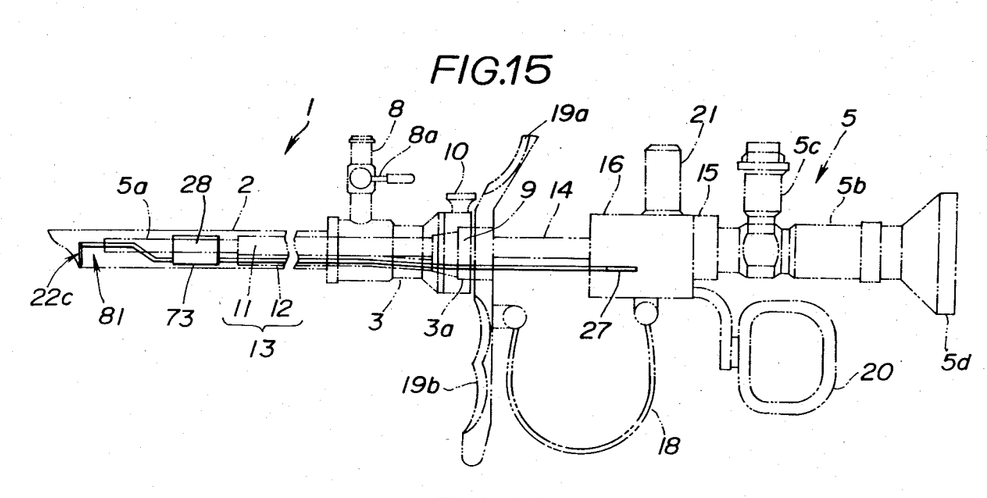
FIG. 15 is a formation view of the entire assembly.
Figure 16:
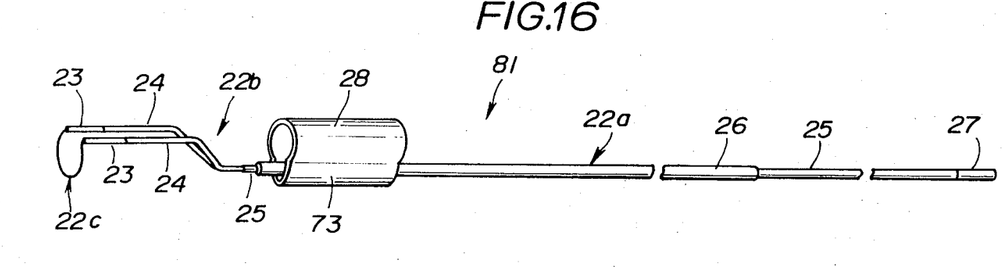
FIG. 16 is a perspective view showing an electrode means.
Figure 17:
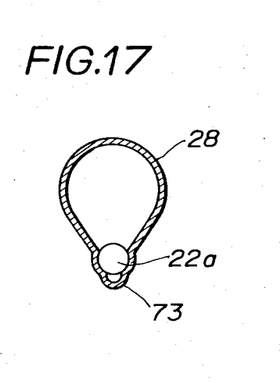
FIG. 17 is a sectioned view showing a stabilizer part of the electrode means.
Figure 18A:
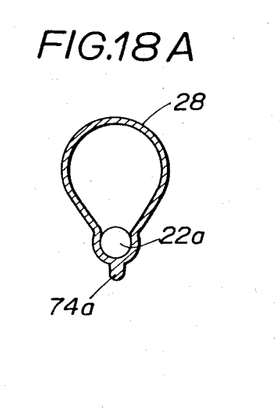
FIGS. 18(A) to (D) are sectioned views showing modifications of a spacer provided in the stabilizer.
Figure 18B:
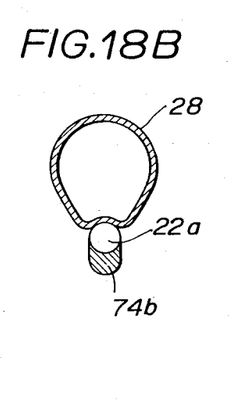
Figure 18C:
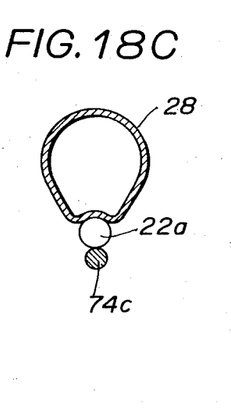
Figure 18D:
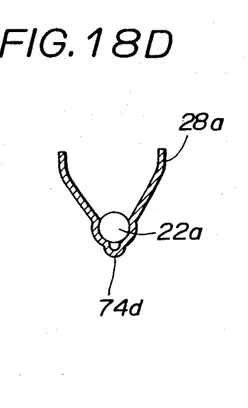

Also, this spacer may be formed as shown in FIGS. 14(A) to (C). That is to say, shown in (A) is a spacer 72a made of a bar-shaped member circular in the cross-section below the stabilizer 28. Shown in (B) is a spacer 72b made of a plate-shaped member tongue-shaped in the cross-section. Shown in (C) is a spacer 72c made of a member arcuate in the cross-section and arranged in the axial direction or at a spot. The above mentioned spacers 72a to 72c are formed also of a metallic material or plastic material or may be molded integrally with the stabilizer 28 by molding or the like.

In the resectoscope device, the electrode means 61 is to be prepared exclusively for each of the sheaths 2 of different thicknesses and the projection amount of each of the spacers 71 and 72a to 72c is to be set to be most adapted to each of the sheaths 2 of different thicknesses so that the position relation of the inside surface of the sheath 2 with the resecting part 22c of the electrode means 61, scope insertion part 5a and handle insertion part 13 may be kept constant or preferably parallel.

FIGS. 15 to 18 relate to the sixth embodiment of the present invention. In this embodiment, the position relation of the shaft part 22a of an electrode means 81 with the scope insertion part 5a is reversed by 180 degrees from the first embodiment. A spacer 73 formed on the stabilizer 28 of this embodiment is formed also in the lower part of the stabilizer 28 and contacts the inside surface of the sheath 2 and the electrode means 81 and scope insertion part 5a are kept at a fixed spacing set always with respect to the inside surface of the sheath 2 or preferably parallel so that the inclination of the electrode means 81, scope insertion part 5a and handle insertion part 13 within the sheath 2 may be prevented. Further, when the projection amount of the spacer 73 of the electrode means 81 to be used for the thickness of each sheath 2 is set to contact the inside surface of the sheath 2, the above mentioned effect will be able to be developed for the sheath 2 of any thickness. The spacer 73 is formed by modifying all or part of the length of the lower side of the substantially cylindrical stabilizer 28.

The spacer may be also formed by such modification as is shown in each of FIGS. 18(A) to (D). The spacer 74a shown in (A) is formed by being molded integrally with the stabilizer 28. The spacer 74b shown in (B) is provided by bonding a plate-shaped member substantially tongue-shaped in the cross-section to the shaft part 22a of the electrode means 81 positioned below the stabilizer 28 independently of the stabilizer 28. The spacer 74c shown in (C) is provided by bonding a bar-shaped member circular in the cross-section to the shaft part 22a of the electrode means in the same manner as in (B). The spacer 74d shown in (D) is formed by modifying to downward project the stabilizer 28a opened above. The material of the above mentioned spacers 73 and 74a to 74d may be a metal or plastic.

In the present invention, the spacer may be provided above the stabilizer part so as to contact the upper inside surface of the sheath.

Also, the spacer may be provided on the inside surface of the sheath so as to contact the stabilizer instead of being provided on the stabilizer part on the electrode means side.

In this invention, it is apparent that embodiments different in a wide range can be formed on the basis of this invention without deviating from the spirit and scope of the invention. This invention is not to be restricted by its specific embodiments except being limited by the appended claims.

We claim:

1. A resectoscope device comprising:
   a sheath body having an elongated hollow sheath to be inserted into a urethra;
   a handle part having a slider connected to said sheath body and sliding in the axial direction;
   an observing scope inserted into said hollow sheath through said handle part and said sheath body;
   an electrode means inserted through said hollow sheath, removably connected at the rear end to said slider, said electrode means having a resecting part for projecting out of and retreating into a beak opening at a tip of said hollow sheath by a sliding operation in the axial direction of said slider, said electrode means having a forked part bent upward at a large angle with the axial direction of a shaft part of said electrode means, and a forward portion of said forked part being inclined forward and upward at a small angle with the axial direction with respect to said shaft part of said electrode means, said shaft part being inserted through said hollow sheath so that, when said resecting part is to be retreated into said beak opening, said forked part will be narrowed and displaced upward by said sliding operation in a rearward direction so that said forked part is housed in contact with an inner upper peripheral surface of the beak above the center axis of the sheath body to prevent said resecting part from catching on an inner lower peripheral surface of the beak; and
   a stabilizer provided in said electrode means, said stabilizer being formed so that said observing scope can be inserted therethrough.

2. A resectoscope device according to claim 1, wherein the shaft part of said electrode means is inserted eccentrically below the sheath body center axis and said stabilizer is fitted above the shaft part near a tip of said shaft part.

3. A resectoscope device according to claim 1 wherein the shaft part of said electrode means is inserted eccentrically above the sheath, said stabilizer is fitted below the shaft part near a tip of said shaft part and the forked part of said electrode means is inclined forward downward from the shaft part and then forward upward.

4. A resectoscope device according to claim 2 wherein the shaft part of said electrode means is formed of two parallel shafts and a plate holding the spacing at a predetermined value is fitted on said two parallel shafts.

5. A resectoscope device according to claim 1 wherein the resecting part of said electrode means is formed to be knife-shaped.

* * * * *